US011026967B2

(12) United States Patent
Ikeda et al.

(10) Patent No.: US 11,026,967 B2
(45) Date of Patent: Jun. 8, 2021

(54) COMPOSITION FOR SUPPRESSING OR PREVENTING ABNORMALITY IN INTESTINAL ENVIRONMENT

(71) Applicants: MiZ Company Limited, Kanagawa (JP); OSAKA UNIVERSITY, Osaka (JP)

(72) Inventors: Mitsunori Ikeda, Osaka (JP); Kentaro Shimizu, Osaka (JP); Hiroshi Ogura, Osaka (JP); Shinichi Hirano, Kanagawa (JP); Ryosuke Kurokawa, Kanagawa (JP)

(73) Assignees: MIZ COMPANY LIMITED, Kanagawa (JP); OSAKA UNIVERSITY, Osaka (JP)

( * ) Notice: Subject to any disclaimer, the term of this patent is extended or adjusted under 35 U.S.C. 154(b) by 0 days.

(21) Appl. No.: 16/085,050

(22) PCT Filed: Mar. 30, 2018

(86) PCT No.: PCT/JP2018/013541
§ 371 (c)(1),
(2) Date: Feb. 4, 2019

(87) PCT Pub. No.: WO2019/123672
PCT Pub. Date: Jun. 27, 2019

(65) Prior Publication Data
US 2019/0183925 A1 Jun. 20, 2019

(51) Int. Cl.
*A61K 33/00* (2006.01)
*A61P 1/00* (2006.01)
*A61K 47/02* (2006.01)

(52) U.S. Cl.
CPC .............. *A61K 33/00* (2013.01); *A61K 47/02* (2013.01); *A61P 1/00* (2018.01)

(58) Field of Classification Search
None
See application file for complete search history.

(56) References Cited

U.S. PATENT DOCUMENTS

| 2015/0258298 A1* | 9/2015 | Satoh | A61K 33/00 128/202.26 |
| 2017/0157045 A1* | 6/2017 | Kurokawa | A61K 9/0095 |

FOREIGN PATENT DOCUMENTS

| JP | 2014-122148 A | 7/2014 |
| JP | 2017-104842 A | 6/2017 |

OTHER PUBLICATIONS

Xie K, Hydrogen gas presents a promising therapeutic strategy for sepsis, BioMed Research International, 2014, 9 pages (Year: 2014).*

Buchholz et al., Hydrogen inhalation ameliorates oxidative stress in transplantation induces intestinal graft injury. *Am. J. Transplant.*, 8:2015-24 (2008).

Chun et al., Effect of enteral glutamine on intestinal permeability and bacterial translocation after abdominal radiation injury in rats, *J. Gastroenterology*, 32(2): 189-195 (1997).

Honda, The Gut Microbiota and Immune System, *Region Fusion Review*, 2:e011 (2013).

Ikeda et al., Controlling intestinal tract failure: effect of high concentration hydrogen water, *J. Jap. Assoc. Acute Med.*, 28(9):439 (2017).

Ishibashi et al., Consumption of water containing a high concentration of molecular hydrogen reduces oxidative stress and disease activity in patients with rheumatoid arthritis: an open-label pilot study, *Medical Gas Research*, 2:27 (2012).

Kanai, Gut microbiota and disease, *J. Jap. Soc. Int. Med.*, 105(9):1695-1700 (2016).

Kayiya et al., Hydrogen mediates suppression of colon inflammation induced by dextran sodium sulfate, *Biochem. Biophys. Res. Commun.*, 386(1):11-15 (2009).

Moore et al., TEN versus TPN following Major Abdominal Trauma—Reduced Septic Morbidity, *J. Trauma*, 29:916-23 (1989).

Nakao et al., Effectiveness of hydrogen rich water on antioxidant status of subjects with potential metabolic syndrome-an open label pilot study, *J. Clin. Biochem. Nutr.* 46:140-9 (2010).

Nakasone et al., Effect of Intake of Molecular Hydrogen-Infused Water on the Status of Obesity in Adult Subjects, A Double-blind, Placebo-controlled, Parallel-group Study, *Jpn. Pharmacol. Ther.*, 45(11):1821-30 (2017).

Ohkusa, Association between Gut Microbiota and Gastrointestinal disease, *Modern Media*, 60(11):325-331 (2014).

Xiao et al., Hydrogen-water ameliorates radiation-induced gastro intestinal toxicity via MyD88' effects on the gut microbiota, *Exper. Molec. Med.* 50:e433 (2018).

Xie et al., Hydrogen Gas Presents a Promising Therapeutic Strategy for Sepsis, *BioMed Res. Internat.*, 1-9 (2014).

Yamamoto et al., Bacterial Translocation : Bacterial Translocation and its clinical significance, 3:336-6 (2006).

Yu et al., Hydrogen-rich saline attenuates eosinophil activation in a guinea pig model of allergic rhinitis via reducing oxidative stress, *J. Inflamm.*, 14(1):s12950 (2017).

Zhang et al., Effect of Hydrogen gas on intestinal Rho/ROCK signaling pathway in septic mice, *Chin. J. Anesthesiol.*, 35(4): 477-480 (2015).

Zhang et al., Effects of hydrogen-rich water on depressive-like behavior in mice, *Sci. Rep.* 6:23742 (2016).

Nakao, "Does hydrogen-rich water really work?", Journal of Okayama Medical Association, vol. 129, pp. 9-15 (Apr. 2017).

Kajiya et al., Hydrogen mediates suppression of colon inflammation induced by dextran sodium sulfate, *Biochem. Biophys. Res. Commun.* 386:11-15 (2009).

(Continued)

*Primary Examiner* — Celeste A Roney
(74) *Attorney, Agent, or Firm* — Brinks Gilson & Lione

(57) ABSTRACT

This application provides a composition comprising hydrogen gas or dissolved hydrogen as an active ingredient for suppressing or preventing abnormality in the intestinal environment of a subject, wherein the abnormality is selected from the group consisting of bacterial translocation and bacterial species composition abnormality of intestinal flora.

10 Claims, 7 Drawing Sheets

Specification includes a Sequence Listing.

(56) References Cited

OTHER PUBLICATIONS

Yamamoto et al., Bacterial Translocation and its clinical significance, *Igaku No Ayumi* (Suppl.) Digestive disease—state of arts I, Digestive Tracts (Esophagus, Gut, Intestine), Ver, 3:33-6 (2006).
Fakai, Y., Hydrogen molecule is pretty amazing, Kobunsha, Tokyo, Japan, Jun. 20, 2020 (Partial Translation).
Ito et al., Drinking hydrogen water and intermittent hydrogen gas exposure, but not lactulose or continuous hydrogen gas exposure, prevent 6-hydorxydopamine-induced Parkinson's disease in rats, *Med. Gas Res*. 2:15 (2012).
Liu et al., Corrigendum: Estimation of the hydrogen concentration in rat tissue using an airtight tube following the administration of hydrogen via various routes, *Sci. Rep*. 4:5485 (2014).

* cited by examiner (A)

(B)

COMPOSITION FOR SUPPRESSING OR PREVENTING ABNORMALITY IN INTESTINAL ENVIRONMENT

RELATED APPLICATIONS

The present patent document is a § 371 filing based on PCT Application Serial No. PCT/JP2018/013541, filed Mar. 30, 2018, which claims priority to Japanese Patent Application Nos. JP 2017-242401, filed Dec. 19, 2017 and JP 2017-242471, filed Dec. 19, 2017, which are hereby incorporated by reference.

TECHNICAL FIELD

The present invention relates to a composition containing hydrogen gas or dissolved hydrogen as an active ingredient for suppressing or preventing abnormality in the intestinal environment of a subject.

Specifically, the abnormality in the intestinal environment is selected from the group consisting of bacterial translocation (BT) and bacterial species composition abnormality of intestinal flora.

BACKGROUND ART

Intestinal flora is present in the intestinal tract, and its homeostasis is important for maintaining health. In recent years, it has been indicated that disturbances of intestinal flora are related to a variety of diseases. In addition, the intestinal tract has an immune system that prevents harmful substances from invading. If the intestinal tract wall barrier is damaged by any cause, harmful substances invade the body and may cause serious diseases. The abnormality thus occurring in the intestinal environment has a risk of harming human health at any time as described below.

Bacterial translocation is a phenomenon in which live or dead bacteria present in the intestinal tract pass through the intestinal tract wall (or intestinal epithelium) due to some cause and migrate from a mesenteric lymph node to a distant organ. Examples of the causes of bacterial translocation include a change in the normal intestinal flora, a decrease in the protection capacity of intestinal epithelial cells, and a decrease in the host immune function.

Examples of the diseases developed or exacerbated by bacterial translocation as a cause or partial cause include infectious diseases of which the sources of the infection cannot be specified, sepsis, systemic inflammatory response syndrome (SIRS) due to high invasion, and multiple organ failure (MOF) syndrome (Non Patent Literature 1).

Accordingly, clinical management for suppressing bacterial translocation is important in prevention of the above-mentioned diseases. However, only a few substances, such as glutamine (Non Patent Literature 2), are known as drugs for suppressing bacterial translocation.

Under such circumstances, the present inventors have focused on hydrogen as a substance for suppressing bacterial translocation. There have been very few reports on the actual clinical effects of hydrogen.

Furthermore, in recent years, it has become obvious that a close relationship is present between bacterial species composition abnormality of intestinal flora (generally called "dysbiosis") and disease. Specifically, about 1000 species of bacteria are present in the human intestinal tract, and the bacterial count is more than one hundred trillion in total. Abnormality in the balance of the composition (or constitution) of bacterial species of the intestinal flora caused by some internal or external factor is associated with development of diseases, such as inflammatory intestinal diseases (e.g., ulcerative colitis and Crohn's disease), gastrointestinal diseases such as irritable bowel syndrome, metabolic syndrome (e.g., diabetes mellitus and arteriosclerosis), metabolic diseases such as obesity, cancer, rheumatic diseases, allergic diseases, and neuropsychiatric disorders (e.g., autism and depression). Accordingly, the outcome of treatment by fecal microbiota transplantation demonstrated that improvement of the bacterial species composition abnormality of intestinal flora can be part of the treatment of the above-mentioned diseases (Non Patent Literatures 3 to 5).

The intestine and the brain are so closely connected that the intestine has even been called the second brain. This connection is due to physiologically active substances, such as short-chain fatty acids (e.g., butyric acid and acetic acid) generated by intestinal bacteria and hormones (e.g., serotonin, dopamine, and precursors thereof). In addition, since the intestine is constantly exposed to invaders (e.g., harmful substances such as pathogens and toxins) from outside the body, a unique immune system has built up. It is believed that an unbalanced bacterial composition of intestinal flora causes abnormal intestinal environment or dysbiosis and disturbs the homeostasis of brain function and immune function and, as a result, partially causes various diseases mentioned above.

Therapy such as fecal microbiota transplantation is known to improve the bacterial species composition abnormality of intestinal flora but is also known to not necessarily be a panacea.

Under such circumstances, this time, the present inventors have found that bacterial translocation can be improved and, in the course of this research, have found a possibility of improving bacterial species composition abnormality of intestinal flora by molecular hydrogen. Proposals involving attempts to use hydrogen gas or hydrogen dissolved in water for treatment of, for example, skin diseases, cancer, and sepsis have been hitherto reported (Patent Literatures 1 and 2 and Non Patent Literature 6). For example, Non Patent Literature 6 describes that inhalation or feeding of hydrogen gas or hydrogen dissolved in water to a sepsis animal model decreases inflammatory cytokines or chemokines and shows beneficial effects on sepsis-related organ damage.

However, there is no report indicating that hydrogen suppresses bacterial translocation and has a possibility of improving bacterial species composition abnormality of intestinal flora.

CITATION LIST

Patent Literature

[Patent Literature 1] Japanese Patent Laid-Open No. 2016-190833
[Patent Literature 2] Japanese Patent Laid-Open No. 2016-113425

Non Patent Literature

[Non Patent Literature 1] Moore F. A., et al., J. Trauma., 29: 916-923, 1989
[Non Patent Literature 2] Chun H., et al., J. Gastroenterology, 32(2): 189-195, 1997
[Non Patent Literature 3] Takanori Kanai, Internal Medicine, 105(9): 1695-1700, 2016 (Japan)
[Non Patent Literature 4] Toshifumi Ohkusa, Modern Media, 60(11): 325-331, 2014 (Japan)

[Non Patent Literature 5] Kenya Honda, Region Fusion Review, 2, e011 (2013); DOI: 10.7875/leading.author.2e011 (Japan)

[Non Patent Literature 6] Xie K., et al., BioMed Research International, Vol. 2014, Article ID 807635, 9 pages

SUMMARY OF INVENTION

Technical Problem

It is an object of the present invention to provide a composition for suppressing, improving, or preventing (or precluding) abnormality in the intestinal environment, in particular, bacterial translocation or bacterial species composition abnormality of intestinal flora.

Suppression or prevention of bacterial translocation leads to suppression of development or exacerbation of the above-mentioned diseases, such as sepsis. Suppression or prevention of bacterial species composition abnormality of intestinal flora is expected to allow preclusion of the development of dysbiosis-related diseases.

Solution to Problem

The present invention includes the following features.

(1) A composition for suppressing or preventing abnormality in the intestinal environment of a subject, the composition comprising hydrogen gas or dissolved hydrogen as an active ingredient, wherein the abnormality is selected from the group consisting of bacterial translocation and bacterial species composition abnormality of intestinal flora.

(2) The composition according to aspect (1), wherein the bacterial translocation leads to development or worsening of sepsis, systemic inflammatory response syndrome (SIRS), or multiple organ failure (MOF) syndrome.

(3) The composition according to aspect (1), wherein the bacterial species composition abnormality is an abnormal increase or decrease in at least one bacterial species in the intestinal flora.

(4) The composition according to aspect (1) or (3), wherein the bacterial species composition abnormality leads to development of a dysbiosis-related disease.

(5) The composition according to any one of aspects (1) to (4), wherein the composition improves intestinal tissue damage of the subject.

(6) The composition according to any one of aspects (1) to (5), wherein the composition is in the form of a hydrogen-containing gas or a hydrogen-dissolved liquid.

(7) The composition according to aspect (6), wherein the hydrogen-containing gas has a hydrogen concentration of 0.5 to 18.5 vol %.

(8) The composition according to aspect (6), wherein the hydrogen-dissolved liquid has a hydrogen concentration of 1 to 10 ppm.

(9) The composition according to any one of aspects (1) to (8), wherein the composition is administered to the subject by a pulmonary route or an oral route.

(10) The composition according to aspect (9), wherein the administration by the pulmonary route is performed in an atmospheric pressure environment or in an environment of a high atmospheric pressure of 1.02 to 7.0 atm.

(11) The composition according to any one of aspects (1) to (10), wherein the composition is produced in situ using a hydrogen gas-supplying apparatus or a hydrogenation device at the time of administration.

The present invention provides novel therapy that can decrease intestinal barrier dysfunction and bacterial species composition abnormality of intestinal flora (dysbiosis) and can preclude or suppress bacterial translocation by administration of dissolved hydrogen or hydrogen gas and is therefore significantly useful for further precluding or suppressing development or worsening of sepsis, systemic inflammatory response syndrome (SIRS), or multiple organ failure (MOF) syndrome and for first-aid treatment or improved prognosis of a patient.

The present invention also provides novel therapy that allows prevention or improvement of bacterial species composition abnormality of intestinal flora by administration of dissolved hydrogen or hydrogen gas and is useful for prevention or relief of various diseases that are expected to occur by bacterial species composition abnormality.

The present specification encompasses the disclosure of Japanese Patent Application No. 2017-242471 (Application date: Dec. 19, 2017) and Japanese Patent Application No. 2017-242401 (Application date: Dec. 19, 2017), based on which the present application claims priority.

DESCRIPTION OF EMBODIMENTS

Figure 1:
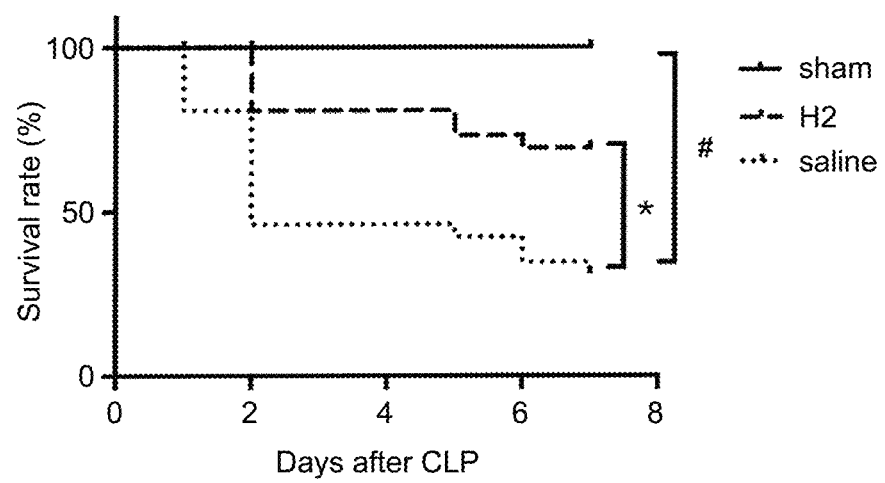
FIG. 1 shows an improvement, by supersaturated hydrogen dissolved saline, in the survival rate in a mouse model of sepsis. In the figure, "sham" indicates a pseudo-group (healthy control without cecal ligation and puncture (CLP) surgery) (n=6), "H2" indicates a supersaturated hydrogen dissolved saline group (n=26), and "saline" indicates a physiological saline (also referred to as "saline") group (n=26). *$p<0.05$, #$p<0.01$ ("p" denotes risk ratio (or also referred to as "significant probability") in a log-rank test).

The present invention will be described in further detail.

The present invention provides a composition comprising hydrogen gas or dissolved hydrogen as an active ingredient for suppressing or preventing abnormality in the intestinal environment of a subject, wherein the abnormality is selected from the group consisting of bacterial translocation and bacterial species composition abnormality of intestinal flora.

Suppression or prevention of bacterial translocation and bacterial species composition abnormality of intestinal flora will now be described.

1. Suppression or Prevention of Bacterial Translocation

As described above, the present invention provides a composition comprising hydrogen gas or dissolved hydrogen as an active ingredient for suppressing or preventing bacterial translocation in a subject and a method for suppressing or preventing bacterial translocation, the method including administration of the composition to a subject.

In the present specification, the term "prevention" with respect to bacterial translocation means that a disease, such as sepsis, caused by bacterial translocation occurring due to some reason in a subject is precluded from developing. The term "suppression" with respect to bacterial translocation means that when a subject has developed a disease, such as sepsis, through bacterial translocation, an increase in the severity (i.e., worsening of symptoms) is improved or avoided by suppressing the bacterial translocation.

In the present specification, the term "bacterial translocation" indicates a phenomenon in which live or dead bacteria present in the intestinal tract pass through the intestinal tract wall (or intestinal epithelium) by any cause and migrate from a mesenteric lymph node to a distant organ. Live or dead bacteria or toxins, such as endotoxin, in some cases enter the blood due to bacterial translocation and go around the whole body to develop sepsis. If the sepsis is further worsened, the sepsis patient develops systemic inflammatory response syndrome (SIRS) or multiple organ failure (MOF) syndrome and dies in some cases. Treatment of sepsis is usually performed by identifying the causative bacteria and administering an agent, such as an antibiotic, effective for the bacteria to the patient.

In human patients with postoperative sepsis, about 60% or more the whole bacteria of the bacterial group reaching mesenteric lymph nodes through bacterial translocation belong to the family Enterobacteriaceae according to the document (O'Boyle C J, et al., Gut, 42: 29-35, 1998). In the bacterial group, the proportion of bacteria of the genus *Escherichia*, in particular, *Escherichia coli*, is the highest, and the bacterial group includes other bacteria, such as bacteria of the genus *Klebsiella*, bacteria of the genus *Proteus*, and bacteria of the genus *Enterobacter*.

As a cause of occurrence of intestinal epithelial permeability of intestinal bacteria, for example, it is described that bacterial translocation is caused by, for example, emergency operation, infectious diseases, inflammatory intestinal diseases, overgrowth of intestinal bacteria, damage of intestinal mucosal tissue, or decrease of immune function (O'Boyle, 1998, mentioned above). The proportion of patients actually developing a disease, such as sepsis, is about 10% to 15%, and the composition of the present invention is effective for suppressing or preventing bacterial translocation in such patients.

Figure 2:
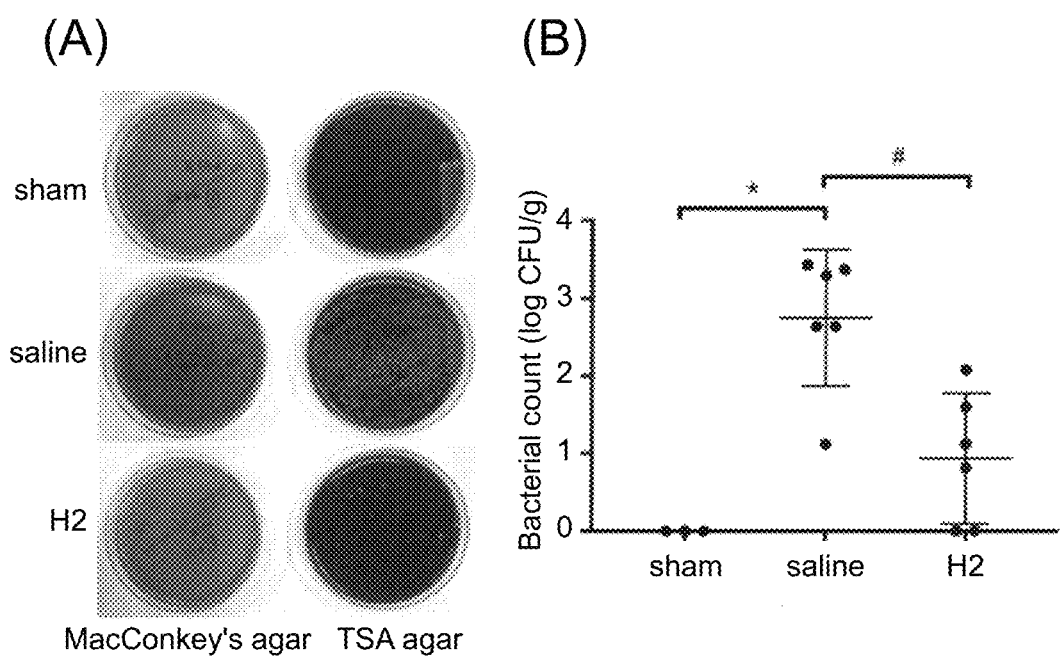
FIG. 2 shows suppression, by supersaturated hydrogen dissolved saline, of bacterial translocation in the mesenteric lymph node (MLN) of a mouse model of sepsis. In the figure, (A) shows cultures when MLNs were aseptically taken out 24 hours after cecal ligation and puncture (CLP) and subjected to plate culture on a MarConkey agar plate or a TSA agar plate for 24 hours; and (B) shows the bacterial count on the MarConkey agar plate expressed by the average ±SD of colony forming unit (log CFU)/g (where "SD" means standard deviation). In the figure, "sham" indicates a pseudo-group (healthy control without CLP surgery), "H2" indicates a supersaturated hydrogen dissolved saline group, and "saline" indicates a physiological saline (also referred to as "saline") group. In each group, n=3 to 6. *$p<0.05$, #$p<0.05$ ("p" denotes risk ratio in a log-rank test).
Figure 3:
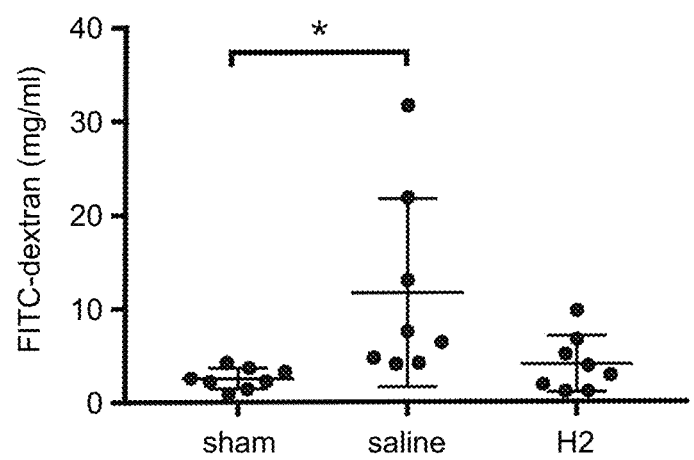
FIG. 3 shows attenuation, by supersaturated hydrogen dissolved saline, of sepsis-related intestinal epithelial hyperpermeability. In the figure, "sham" indicates a pseudo-group (healthy control without CLP surgery), "H2" indicates a supersaturated hydrogen dissolved saline group, and "saline" indicates a physiological saline (also referred to as "saline") group. In each group, n=8. *$p<0.05$ ("p" denotes risk ratio in a log-rank test).

According to the present invention, bacterial translocation can be thus suppressed or prevented by administering hydrogen gas or a dissolved hydrogen liquid to a subject. This fact is also obvious from evidence that, as shown in FIG. 2, the intestinal bacterial count in mesenteric lymph nodes (MLNs) of a mouse model is decreased and that, as shown in FIG. 3, the hyper-permeability of intestinal bacteria from the intestinal epithelium is decreased.

A possibility of hydrogen gas or a dissolved hydrogen liquid as a therapeutic agent for sepsis has been hitherto indicated (Non Patent Literature 6). Specifically, it has been reported that, for example, hydrogen has anti-inflammatory action because it decreases the levels of inflammatory cytokine and chemokine in serum or tissue of a patient and has antioxidation action because it reduces oxidative damage of tissue. However, it has not been hitherto known that hydrogen itself has an ability of suppressing or precluding bacterial translocation.

As described above, according to the present invention, if bacterial translocation can be suppressed or precluded, it is possible to further suppress or preclude development or worsening of sepsis, systemic inflammatory response syndrome (SIRS), or multiple organ failure (MOF) syndrome. Accordingly, the composition of the present invention can preclude these diseases from developing or can preclude or suppress sepsis from becoming severe to SIRS or MOF. As shown in FIG. 1, the survival rate is significantly improved by administering a dissolved hydrogen liquid to a mouse model of sepsis.

Figure 5:
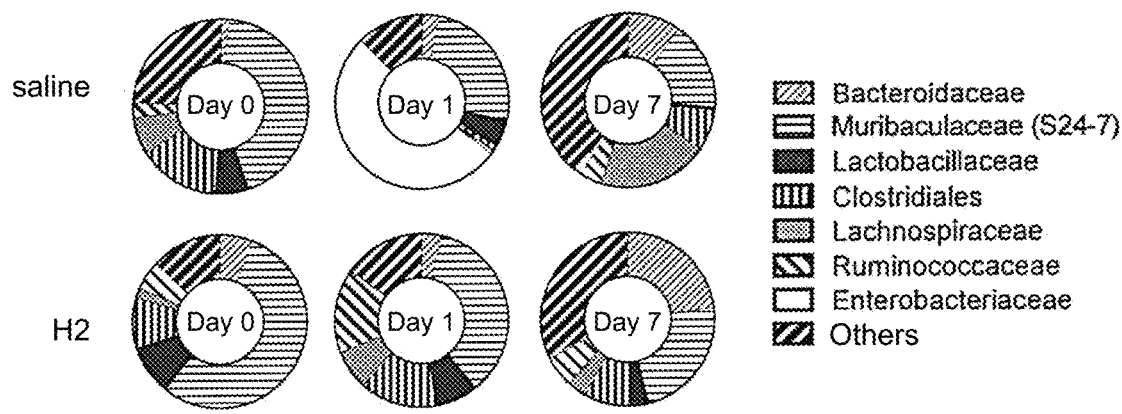
FIG. 5 shows suppression, by supersaturated hydrogen dissolved saline, of excessive growth of enterobacteria in the intestine of a mouse model of sepsis. In the figure, (A) shows a continuous change in the intestinal bacteria composition on the day of cecal ligation and puncture (CLP) (Day 0) and the 1st day (Day 1) and the 7th day (Day 7) after CLP; and (B) shows the quantitative results (log (number of bacteria)/g feces) of the number of enterobacteria for 1 g of mouse feces on Day 0 and Day 1 after the cecal ligation and puncture (CLP). The data are shown as the average±SD, and n=8 in each group. In the figure, "H2" indicates a supersaturated hydrogen dissolved saline group, and "saline" indicates a physiological saline (also referred to as "saline") group.
Figure 5:
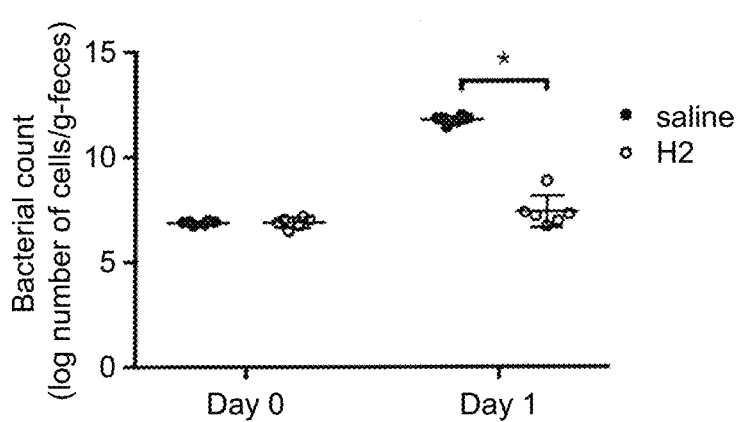

Thus, the actions of hydrogen as an active ingredient of the composition of the present invention, for example, the action of improving intestinal tissue damage of a subject and the action of suppressing overgrowth of some bacterial species, such as bad bacteria (e.g., Enterobacteriaceae bacteria) in the intestinal flora of a subject, are thought to significantly work to suppress or preclude development of sepsis or worsening of developed sepsis. Overgrowth of Enterobacteriaceae bacteria is also observed in a mouse model of sepsis as shown in FIG. 5. This will be specifically described in section 2. below.

Figure 4:
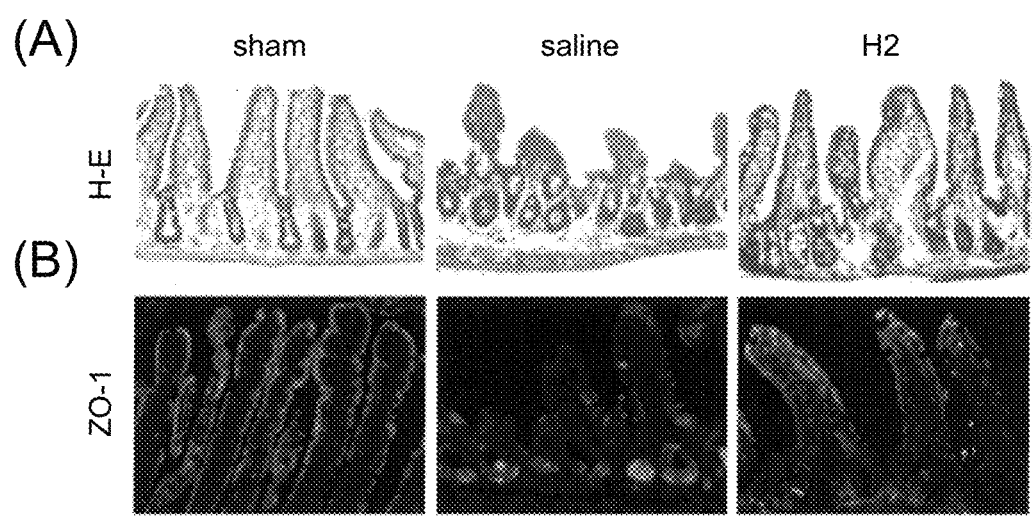
FIG. 4 shows protection (A) of a mouse model of sepsis from morphological intestinal damage by supersaturated hydrogen dissolved saline and localization (B) of tight junction protein (ZO-1): (A) microscopic image (×200 magnification) of hematoxylin-eosin (H-E) stained small intestine (terminal ileum) 24 hours after cecal ligation and puncture (CLP); and (B) fluorescent antibody-stained microscopic image (×400 magnification, the bright green spot (brightly luminescent portion) indicates ZO-1, and the blue (dark portion) indicates nuclei). In the figure, "sham" indicates a pseudo-group (healthy control without CLP surgery), "H2" indicates a supersaturated hydrogen dissolved saline group, and "saline" indicates a physiological saline (also referred to as "saline") group.
Figure 6:
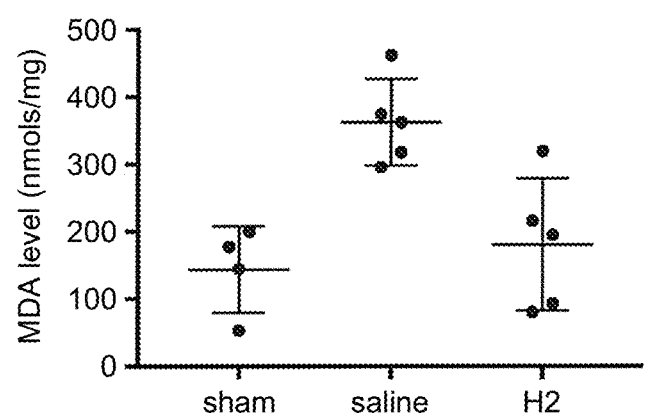
FIG. 6 shows a reduction, by supersaturated hydrogen dissolved saline, in the oxidative stress of the intestine of a mouse model of sepsis. The degree of oxidative stress is expressed by quantitation of the intestinal malondialdehyde (MDA) level (nmol/mg intestinal tissue). The data are shown as the average±SD, and n=4 to 5 in each group. p<0.05 ("p" denotes risk ratio in a log-rank test). In the figure, "sham" indicates a pseudo-group (healthy control without CLP surgery), "H2" indicates a supersaturated hydrogen dissolved saline group, and "saline" indicates a physiological saline (also referred to as "saline") group.
Figure 7:
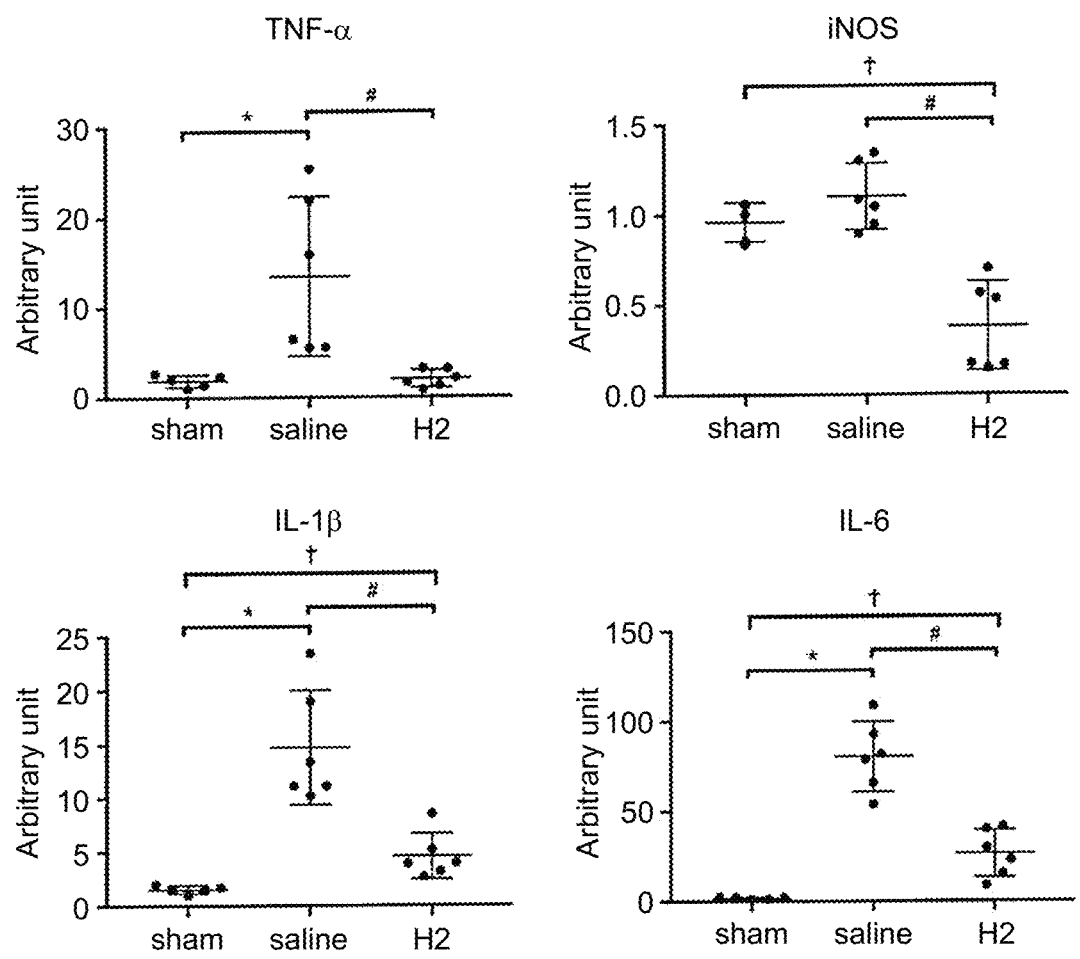
FIG. 7 shows a decrease, by supersaturated hydrogen dissolved saline, in the inflammatory response in the intestinal tissue of a mouse model of sepsis. Expression levels (arbitrary unit) of inflammatory mediators: tumor necrosis factor α (TNF-α), inducible nitric oxide synthase (iNOS), interleukin 1β (IL-1β), and interleukin 6 (IL-6), in the small intestine (terminal ileum) measured by quantitative RT-PCR analysis are shown. The data are shown as the average±SD, and n=5 or 6 in each group. *p<0.05, #p<0.05, †p<0.05 (where "p" denotes risk ratio in a log-rank test). In the figure, "sham" indicates a pseudo-group (healthy control without CLP surgery), "H2" indicates a supersaturated hydrogen dissolved saline group, and "saline" indicates a physiological saline (also referred to as "saline") group as a control.

Furthermore, regarding improvement of intestinal tissue damage, a decrease in the MDA level after treatment with hydrogen as shown in FIG. 6, i.e., a reduction in oxidative stress, decreases in the levels of inflammatory mediators (such as TNF-$\alpha$, iNOS, IL-1$\beta$, and IL-6) in intestinal tissue after treatment with hydrogen as shown in FIG. 7, and protection from morphological intestinal damage of a mouse model of sepsis and localization of tight junction protein (ZO-1) as shown in FIG. 4 are clearly proved. The inflammatory mediators are released from macrophages or vascular endothelial cells infiltrated into the inflammatory site of tissue and cause, for example, hyper-vascular permeability, apoptosis, or tissue destruction.

2. Suppression or Prevention of Bacterial Species Composition Abnormality of Intestinal Flora The present invention also provides a composition comprising hydrogen gas or dissolved hydrogen as an active ingredient for suppressing or preventing bacterial species composition abnormality of intestinal flora in a subject and a method for suppressing or preventing bacterial species composition abnormality of intestinal flora, the method including administration of the composition to a subject.

The present invention is, as described below, based on the finding that hydrogen gas or dissolved hydrogen allows preclusion or improvement of bacterial species composition abnormality of intestinal flora in a subject.

In the present specification, the term "bacterial species composition abnormality of intestinal flora" indicates abnormality of the bacterial species composition (or constitution) of intestinal flora, wherein the composition is obviously different from that of a healthy individual and the difference is related to a specific disease. Accordingly, the bacterial species composition abnormality of intestinal flora is an abnormal increase or decrease of at least one bacterial species in intestinal flora or can develop a dysbiosis-related disease.

It is said that an individual having any genetic predisposition (e.g., a genetic predisposition resulted from a predisposition to obesity or a predisposition to development of a disease such as type 2 diabetes mellitus or an inflammatory intestinal disease) breaks the balance of bacterial composition of intestinal flora by, for example, deterioration of any environmental factor and breaks the homeostasis of intestinal ecosystem to cause development or exacerbation of various diseases (Ohno H., Jpn. J. Clin. Immunol., 37(5): 403-411, 2014). Although intestinal bacteria generate various metabolic products depending on the species to maintain the physical health or homeostasis of the body, it is known, for example, that a decrease of a bacterial group generating short-chain fatty acids, such as butyric acid, readily causes, for example, obesity or type 2 diabetes mellitus, that a decrease of Bifidobacterium, which is a good bacterium, decreases the generation of short-chain fatty acids, such as lactic acid and acetic acid, to readily develop infectious diseases due to pathogenic bacteria, and that bacteria generating serotonin, dopamine, or a precursor are decreased to develop depression. Butyric acid generated by intestinal bacteria is known to induce colonic regulatory T cells (Treg) and is said to be involved in suppression of pathological immune response, such as allergy, by negatively controlling abnormal or excessive immune response. Thus, bacterial species composition abnormality of intestinal flora causes a variety of diseases.

Suppression or prevention of bacterial species composition abnormality of intestinal flora is, as demonstrated by the mouse model of sepsis shown in FIG. 5, obvious from evidence that an abnormal increase of Enterobacteriaceae bacteria in the intestinal flora of a subject is dramatically suppressed by administration of hydrogen gas or a dissolved hydrogen liquid. The abnormal increase of the bacteria, which is probably caused by sepsis, was precluded by administration of hydrogen, but the mechanism thereof is unclear.

According to the document (O'Boyle C J, mentioned above), in human patients with postoperative sepsis, about 60% or more the whole bacteria of the bacterial group reaching mesenteric lymph nodes through bacterial translocation (bacteria excessively permeate through intestinal epithelium cells, arrive at mesenteric lymph nodes, and further migrate to a distant organ) belong to the family Enterobacteriaceae.

Administration of hydrogen can also achieve advantageous effects such as suppression of bacterial translocation, relief of intestinal mucosal tissue damage, a decrease in the expression of inflammatory cytokine, and a reduction in oxidative stress (see Examples described below). Thus, hydrogen prevents bacteria from permeating through intestinal epithelium and further migrating to the whole body and protects organ tissue including intestine and therefore allows relief or improvement of the disease developed by bacterial species composition abnormality of intestinal flora.

Specifically, hydrogen can improve intestinal tissue damage due to an intestinal disease (e.g., an inflammatory intestinal disease) developed by, for example, bacterial species composition abnormality of intestinal flora. Regarding such improvement action in a subject, as in section 1. described above, for example, a decrease in the MDA level after treatment with hydrogen as shown in FIG. 6, i.e., a reduction in oxidative stress, decreases in the levels of inflammatory mediators (such as TNF-$\alpha$, iNOS, IL-1$\beta$, and IL-6) in intestinal tissue after treatment with hydrogen as shown in FIG. 7, and protection from morphological intestinal damage of a mouse model of sepsis and localization of tight junction protein (ZO-1) as shown in FIG. 4 are clearly proved. It is well known that the inflammatory mediators are released from macrophages or vascular endothelial cells infiltrated into the inflammatory site of tissue and cause, for example, hyper-vascular permeability, apoptosis, or tissue destruction.

In the present invention, the term "bacterial species composition abnormality of intestinal flora" indicates abnormality in which the balance of bacterial composition is broken and the homeostasis of intestinal ecosystem (i.e., environmental system based on the interaction between the host intestinal tract and intestinal flora) is broken to develop or exacerbate a variety of diseases. Specifically, the bacterial species composition abnormality is caused by, for example, obesity, diabetes mellitus, allergy, a decrease of bacteria generating short-chain fatty acids (e.g., butyric acid and acetic acid) associated with intestinal barrier function and so on, an increase of bacteria generating carcinogenic substances, and a decrease of bacteria generating hormones or precursors of the hormones functioning in the brain.

It has not been hitherto known that hydrogen gas or a dissolved hydrogen liquid has an ability of suppressing or preventing bacterial species composition abnormality of intestinal flora.

The suppression or prevention of bacterial species composition abnormality of intestinal flora by the present invention allows prevention, relief, or improvement of diseases that are developed by the bacterial species composition abnormality, for example, inflammatory intestinal diseases (e.g., ulcerative colitis and Crohn's disease), gastrointestinal diseases such as irritable bowel syndrome, metabolic syndrome (e.g., type 2 diabetes mellitus and arteriosclerosis), metabolic diseases such as obesity, cancer, rheumatic diseases (e.g., rheumatoid arthritis), neuropsychiatric disorders (e.g., autism, depression, and Parkinson's disease), and allergic diseases.

The bacterial composition of intestinal flora is analyzed by amplifying bacterial DNA extracted from feces by PCR, further amplifying the V region (e.g., V1-V2 or V3-V4) of 16S rRNA gene by PCR, purifying the amplified product to prepare a library, and then adding a high-throughput sequencing adapter sequence to determine the sequence using a next generation sequencer. The determined sequence is subjected to homology search against 16S rRNA database and to phylogenetic classification analysis. Furthermore, the difference of bacterial flora can be determined by a method, such as principal coordinates analysis (PCoA) or relative comparison of the bacterial counts of classified bacterial group (e.g., Kamo T., et al., PLoS ONE, 12(3): e0174099, 2017; Nishijima S., et al., DNA Research, 2382: 126-133, 2016).

3. Composition

The hydrogen gas or dissolved hydrogen as an active ingredient of the composition of the present invention is preferably in the form of a hydrogen-containing gas or a hydrogen-dissolved liquid.

The hydrogen-containing gas is preferably air containing hydrogen gas or a gas mixture containing hydrogen gas and oxygen gas. The concentration of hydrogen gas in the hydrogen-containing gas is higher than zero (0) and 18.5 vol % or less such as 0.5 to 18.5 vol %, preferably 1 to 10 vol % such as 2 to 8 vol % or 3 to 6 vol %, and more preferably 4 to 6 vol % such as 4 to 5 vol %. When the gas other than hydrogen gas is air, the concentration of the air is, for example, within a range of 81.5 to 99.5 vol %. When the gas other than hydrogen gas is a gas containing oxygen gas, the concentration of the oxygen gas is, for example, within a range of 21 to 99.5 vol %, and the other main gas can be nitrogen gas, and a gas contained in air, such as carbon dioxide, may be contained in an amount equivalent to that in air. In any case, since hydrogen is a combustible and explosive gas, the amount of hydrogen contained in the composition should be a level safe for a subject, such as a human, to which the composition is administered.

The hydrogen-dissolved liquid is specifically an aqueous liquid in which hydrogen gas is dissolved. Herein, the aqueous liquid is, for example, water, physiological saline, a buffer (e.g., a buffer of pH 4 to 7.4), ethanol-containing water (e.g., ethanol content of 0.1 to 2 vol %), infusion, injection solution, transfusion, or drink. The hydrogen concentration of the hydrogen-dissolved liquid is, for example, 1 to 10 ppm, preferably 2 to 8 ppm, and further preferably 3 to 7 ppm.

The hydrogen-containing gas or the hydrogen-dissolved liquid is adjusted to a predetermined hydrogen gas concentration and is then packed in a pressure resistant container (e.g., an aluminum can, pressure-resistant plastic can or bag, or pressure-resistant PET bottle). Alternatively, the hydrogen-containing gas or the hydrogen-dissolved liquid may be produced in situ using a known hydrogen gas-supplying apparatus or hydrogenation device at the time of administration.

The hydrogen gas-supplying apparatus can mix hydrogen gas generated by a reaction between a hydrogen-generating agent (e.g., metallic aluminum) and water with dilution gas (e.g., air or oxygen) at a predetermined ratio (e.g., Japanese Patent No. 5228142). Alternatively, hydrogen gas generated through electrolysis of water is mixed with dilution gas (e.g., Japanese Patent Nos. 5502973 and 5900688). Consequently, a hydrogen-containing gas having a hydrogen concentration within a range of 0.5 to 18.5 vol % can be prepared.

The hydrogenation device generates hydrogen using a hydrogen-generating agent and a pH adjuster and dissolves the hydrogen in a biocompatible liquid such as water (e.g., Japanese Patent Nos. 4756102, 4652479, 4950352, 6159462, and 6170605). The combination of the hydrogen-generating agent and the pH adjuster is, for example, a combination of metallic magnesium and strong acid ion-exchange resin or organic acid (e.g., malic acid or citric acid) or a combination of metallic aluminum powder and calcium hydroxide powder. Consequently, a hydrogen-dissolved liquid having a dissolved hydrogen concentration of about 1 to 10 ppm can be prepared.

The method for administering the composition of the present invention to a subject is preferably pulmonary administration, such as inhalation or suction, when the active ingredient is hydrogen gas and is preferably oral administration when the active ingredient is a dissolved hydrogen liquid. In the case of inhalation of gas, the gas can be inhaled from the mouth or nose to the lung via a mask-type device covering the mouth and nose and can be delivered to the whole body via the blood. In the case of oral administration of a dissolved hydrogen liquid, the liquid is preferably stored at low temperature, and the cooled liquid may be administered to a subject. Alternatively, when the dissolved hydrogen liquid is in the form of infusion or injection solution, the liquid may be administered to a subject by a parenteral route, such as intravenous administration or intraarterial administration.

A hydrogen-containing gas having the above-mentioned hydrogen concentration or a hydrogen-dissolved liquid having the above-mentioned dissolved hydrogen concentration can be administered to a subject once or several times (e.g., two to three times) per day over one week to 6 months or more, preferably 2 weeks to 3 months. In administration of a hydrogen-containing gas, the gas can be administered over, for example, 10 minutes to 2 hours or more, preferably 20 to 40 minutes per once. In pulmonary administration of a hydrogen-containing gas by inhalation or suction, the gas can be administered to a subject in an atmospheric pressure environment or in an environment of, for example, a high atmospheric pressure within a range of higher than standard atmospheric pressure (referring to about 1.013 atm) and not higher than 7.0 atm, for example, 1.02 to 7.0 atm, preferably 1.02 to 5.0 atm, more preferably 1.02 to 4.0 atm, and further preferably 1.02 to 1.35 atm. Administration in a high atmospheric pressure environment facilitates the absorption of hydrogen in the body of the subject.

The high atmospheric pressure environment can be formed by using a high-atmospheric pressure housing (for example, capsule-type housing) designed so as to have a strength sufficient for forming a high atmospheric pressure of higher than standard atmospheric pressure and not higher than 7.0 atm in the housing by, for example, press fitting the hydrogen-containing gas or air. The high-atmospheric pressure housing preferably has a round shape with no corners as a whole for being pressure resistant. The material of the high-atmospheric pressure housing is preferably lightweight and strong, and examples thereof include reinforced plastics, carbon fiber composite materials, titanium alloys, and aluminum alloys. A subject can be administered the composition containing hydrogen gas together with oxygen gas or air in a high-atmospheric pressure capsule.

The term "subject" in the present specification includes mammals, for example, primates including humans, pet animals such as dogs and cats, and ornamental animals such as animals in zoos. A preferred subject is a human.

EXAMPLES

Although the present invention will be further specifically described with reference to the following Examples, the scope of the present invention is not limited to the Examples.

Example 1

<Suppression or Improvement of Abnormality in Intestinal Environment, Bacterial Translocation and/or Bacterial Species Composition Abnormality of Intestinal Flora, by Administration of Hydrogen Gas-Dissolved Liquid>
I. Experiment
[1] Animal Model of Sepsis Six-week old male C57/BL6 mice having a body weight of 20 to 25 g were subjected to cecal ligation and puncture (CLP) to produce a model of sepsis. Briefly, the mice were anesthetized, and the cecum was exposed by abdomen median incision of 1 cm. A site 1 cm away from the upper end of the cecum was ligated, and moderate CLP (note: 40% mice survived for 7 days) was carried out by stabbing one position of the cecum with a 23-gauge needle to cause puncture. The cecum was returned to the abdomen, and the incision was sutured. Immediately thereafter, all mice were resuscitated by subcutaneous injection of saline (50 mL/kg body weight).

[2] Experiment Protocol

The protocol of this experiment was performed in a pseudo-group (sham), a saline-treating group (saline), and a supersaturated hydrogen dissolved saline-treating group (H2). The pseudo-group was a healthy control without CLP surgery. The saline-treating group was forcibly fed with 15 mL/kg saline per day for seven days. The H2 group was forcibly fed with 15 mL/kg supersaturated hydrogen dissolved saline per day for seven days. The supersaturated hydrogen dissolved saline was produced as a 7 ppm hydrogen gas-dissolved liquid according to the process of a manufacturer (MiZ Co., Ltd., Japan).

[Intestinal Permeability]

In order to determine the intestinal epithelial permeability, the amount of 4.4 kDa fluorescein isothiocyanate-labeled dextran (FITC-dextran: Sigma-Aldrich), which has been traditionally used for evaluating intestinal mucosa permeability, appeared in blood was measured. For the measurement, 0.2 mL of 25 mg/mL FITC-dextran in phosphate buffered saline (PBS) was forcibly fed to the mice 21 hours after pseudo-treatment or CLP treatment. Three hours later, blood samples were collected from the mice by cardiac puncture. The blood was centrifuged at 3000×g for 10 minutes at 4° C., and the plasma was measured with SH9000 Lab fluorescence microplate reader (Corona Electric Co., Ltd.) at an excitation wavelength of 480 nm and an emission wavelength of 520 nm. The concentration of FITC-dextran in the plasma was measured using a dilution-series of FITC-dextran as the standard.

[Measurement of Bacterial Translocation]

The bacterial translocation was evaluated according to the method described in the document (Deitch E A, et al., J. Clin. Invest. 84: 36-42, 1989). Briefly, five or six mesenteric lymph nodes (MLNs) were aseptically taken out 24 hours after CLP, and the weight thereof was measured. The MLNs were homogenized in PBS into a concentration of 50 mg/mL. Ten-fold serial dilution suspensions were subjected to plate culture on a trypsin-treated soy agar (TSA) plate containing 5% sheep blood and on a MarConkey agar plate to grow all bacteria and Gram-negative bacteria, respectively. The two plates were subjected to anaerobic culture in an incubator of 37° C. for 24 hours, and the number of colonies was then counted. The bacterial count in the MLNs was expressed by the colony forming unit (CFU) per g of MLN tissue.

[Histological Analysis]

The mice were sacrificed 24 hours after CLP and were subjected to transcardial perfusion with PBS and then 4% paraformaldehyde in 0.1 M phosphate buffer (PB). The small intestine (terminal ileum) was resected and was immersed in the same fixing solution and cooled and protected in a series of sucrose solutions (15%, 20%, and 25% sucrose in 0.1 M PB) at 4° C. for 3 days. The samples were frozen in an OCT compound (Sakura Finetechnical Co., Ltd.) and were then sliced into slices of 82 μm thickness with a cryostat (CM3050S, Leica Microsystems GmbH), and the cooled slices were stained with hematoxylin and eosin.

[Fluorescent Antibody Method]

The cooled slices were blocked with 20% Block Ace (Sumitomo Dainippon Pharma Co., Ltd.) in 0.1 M PB containing 0.005% saponin and were incubated with a rat monoclonal antibody against tight junction-1 (ZO-1) (Santa Cruz Biotechnology, Inc.) at 4° C. overnight. On this occasion, the antibody was diluted with 1% normal goat serum in PBS to 1:200. The slices were washed in PBS three times and were then incubated together with a 500-fold diluted Alexa Fluor 488-conjugated goat anti-rabbit IgG antibody (Invitrogen) and DAPI (Sigma-Aldrich) at room temperature for 1 hour. After each reaction, the slices were washed with PBS. Ultimately, the slices were fixed with SlowFade reagent (Invitrogen). Subsequently, images were observed with a fluorescence microscope apparatus (Olympus Corporation, Japan).

[Statistical Analysis]

Data are shown as the average±standard deviation (SD). Differences between experimental groups were determined by ANOVA using a Tukey's post hoc comparison test. Survival rates were analyzed by a Kaplan-Meier method, and differences between groups were compared by a log-rank test. Statistical analysis was carried out using Graph Pad Prism 7.0 (Graph Pad Software, Inc.), and $p < 0.05$ was considered significant.

[Measurement of Microbiome By 16S rRNA Sequencing]

Fecal samples were collected from mice on day 0, day 1, day 3, and day 7 after CLP, and microbiome was measured. Specifically, DNA was extracted from a fecal sample using a PowerSoil DNA extraction kit (MOBIO), and PCR was performed using KAPA HiFi HotStart Ready Mix (KAPA Biosystems). The primer set used for the PCR consisted of 784F: 5'-AGGATTAGATACCCTGGT-3' (SEQ ID NO: 1)

and 1061R: 5'-CRRCACGAGCTGACGAC-3'(SEQ ID NO: 2, herein R=A or G), and the target was the V5-V6 region of 16S rRNA gene (Andersson A F, et al., PLoS One 3: e2836, 2008). A DNA library was produced using an Ion PGM Sequencing Hi-Q kit (Life Technologies Corporation) according to the manual of the manufacturer. Sequencing was performed using two 318 chips and an Ion PGM Sequencing Hi-Q kit (Life Technologies Corporation) on an Ion PGM sequencer (Life Technologies Corporation). The determined sequence was analyzed with QIIME pipeline (Caoraso J G, et al., Nat. Methods 7: 335-336, 2010).

[Quantitative Analysis of Enterobacteriaceae Bacteria]

Each fecal sample for nucleic acid extraction was weighed and suspended in 9 volumes of PBS(−) to prepare a fecal homogenate (100 mg feces/mL). The bacterial DNA was extracted according to a known method (Matsuki T., et al., Appl. Environ. Microbiol. 70: 167-173, 2004). Briefly, glass beads (0.3 g, diameter: 0.1 mm, BioSpec Products, Inc.), 300 μL of Tris-SDS solution, and 500 μL of TE-saturated phenol were added to 200 μL of fecal homogenate or bacterial culture. The mixture was vortexed vigorously for 30 seconds with a FastPrep-24 homogenizer (M. P. Biomedicals) at a power level of 5.0. After centrifugation of the mixture at 4° C. at 2000×g for 5 minutes, 400 μL of the suspension was collected and an equal volume of phenol-chloroform-isoamyl alcohol (25:24:1) was added to the supernatant. After further centrifugation at 4° C. at 2000×g for 5 minutes, 250 μL of the suspension was collected and was subjected to isopropanol precipitation. Finally, the precipitate was suspended in 200 μL of TE buffer and was stored at −30° C. Quantitative real-time PCR (qPCR) was performed with GoTaq qPCR Master Mix (Promega Corporation), and the amount of bacterial rRNA gene was measured with an ABI PRISM 7900HT sequence detection system (Applied Biosystems). A primer set, En-lsu-3F: 5'-TGCCGTACTTCGGGAGAAGGCA-3' (SEQ ID NO: 3) and En-lsu-3'R: 5'-TCAAGGACCAGTGTTCAGTGTC-3' (SEQ ID NO: 4) (Kurakawa T., et al., J. Microbiol. Methods, 92(2): 213-219, 2013), specific to the family Enterobacteriaceae was used. In each reaction, the concentration of each primer was 1 μM. The amplification program consisted of one cycle at 95° C. for 5 minutes, followed by multiple cycles at 94° C. for 20 seconds, 55° C. for 20 seconds, and 72° C. for 50 seconds. The fluorescent product was detected in the last step of each cycle. A melting curve analysis was performed after the amplification to distinguish the targeted PCR product from non-targeted products. The melting curve was obtained by slow heating at temperature of 60° C. to 95° C. at a rate of 0.2° C/sec with continuous fluorescence collection. The qPCR amplification and detection were performed in a 384-well optical plate with an ABI PRISM 7900HT sequence detection system (Applied Biosystems). The standard curve was generated using the quantification cycle (Cq) value of the DNA extracted from *E. coli* JCM1649. The bacterial count of this bacterium strain was measured by microscopic observation using the DAPI staining method described in the document (Jansen G. J., et al., J. Microbiol. Methods, 37: 215-221, 1999). The Cq values in the linear range of the assay were applied to the analytical curve generated in the same experiment to obtain the corresponding bacterial count in each nucleic acid sample; this bacterial count was then converted to the bacterial count per sample.

[Expression of mRNA of Intestinal Inflammatory Mediator by RT-PCR]

In order to evaluate inflammatory mediators, such as iNOS, quantification cycle tumor necrosis factor α (TNF-α), interleukin 6 (IL-6), and interleukin 1β (IL-1β), in the small intestine (terminal ileum), the mRNAs expression thereof was obtained 6 hours after CLP. Total RNA was extracted from a tissue sample and was reverse-transcribed to cDNA using a High-Capacity cDNA Reverse Transcription Kit (Life Technologies Corporation) according to the protocol of the manufacturer. RT-PCR was performed using Fast SYBR Green Master Mix on a StepOne Plus real-time PCR cycler (Applied Biosystems). The specific primers used are collectively shown in Table 1.

TABLE 1

| Gene | Primer | | SEQ ID NO. | Amplified nucleotide length (bp) |
|---|---|---|---|---|
| iNOS | forward | GGCAGCCTGTGAGACCTTTG | 5 | 72 |
| | reverse | GCATTGGAAGTGAAGCGTTTC | 6 | — |
| TNF-α | forward | GAGAAGAGGCTGAGACATAGGC | 7 | 169 |
| | reverse | GGTTCTGTCCCTTTCACTCACT | 8 | — |
| IL-1β | forward | TTTGAAGTTGACGGACCCC | 9 | 148 |
| | reverse | ATCTCCACAGCCACAATGAGTG | 10 | — |
| IL-6 | forward | TCGGAGGCTTAATTACACATGTTC | 11 | 66 |
| | reverse | TGCCATTGCACAACTCTTTTCT | 12 | — | iNOS: inducible nitric oxide synthase
TNF-α: tumor necrosis factor-α
IL-1β: interleukin-1β
IL-6: interleukin-6

The PCR product was amplified (95° C. for 3 seconds, 60° C. for 30 seconds, 45 cycles) and was detected on Step One Plus (Applied Biosystems). The mRNA expression level is relative to β-actin level.

[Evaluation of Oxidative Stress]

In order to measure oxidative stress, the tissue malondialdehyde (MDA) level was measured at 6 hours after CLP. The MDA level was assayed for observing lipid peroxidation product by measuring the thiobarbituric acid reactive substance level. Each tissue sample was quickly frozen to −80° C. and was aliquoted into 50 μg samples. The samples were each homogenized in RIPA buffer (FUJIFILM Wako Pure Chemical Corporation) to preclude oxidation of the samples. All samples were centrifuged (4° C., 10,000×g, 10 minutes), and the supernatant was collected and was evaluated with an OxiSelect TBARS Assay Kit (Cell Biolabs, Inc.) according to the manual of the manufacturer. Absorbance at 532 nm was measured with a NanoDrop spectrophotometer (Thermo Fisher Scientific). The MDA concentration was expressed as nmol per mg of protein (nmol/mg).

II. Results

[Improvement in Survival By Supersaturated Hydrogen Dissolved Saline]

In order to investigate whether supersaturated hydrogen dissolved saline can improve the survival rate in sepsis mice, 15 mL/kg of supersaturated hydrogen dissolved saline was fed to the mice every day for 7 days after CLP surgery. FIG. 1 shows survival curves. The survival rates during the experimental period of 7 days were 100% in the pseudo-group (n=10), 31% in the saline group (n=26), and 69% in the H2 group (n=26). The survival rate in the H2 group was significantly higher than that of the saline group (p<0.01).

[Preclusion of Bacterial Translocation by Supersaturated Hydrogen Dissolved Saline]

In the analysis of MLN culture, the numbers of colonies on a TSA agar plate and a MacConkey agar plate were counted 24 hours after CLP to determine whether bacterial translocation occurred or not. In the pseudo-group, no colonies were observed. In the saline group, colonies were formed on the TSA and MacConkey agar plate, but in the H2 group, although colonies were present, the formation was suppressed (FIG. 2A). In the H2 group, a considerable decrease in the number of colonies present on the MacConkey agar plate was observed, compared to the saline group ($p<0.05$) (FIG. 2B).

[Attenuation of Hyper-Permeability Through Intestine by Supersaturated Hydrogen Dissolved Saline]

The intestinal permeability was evaluated by measuring the appearance of FITC-dextran in plasma 24 hours after CLP. As a result, the level of FITC-dextran was significantly high in the saline group, compared with the pseudo-group, and was attenuated in the H2 group (FIG. 3).

[Relief of Morphological Intestinal Damage by Supersaturated Hydrogen Dissolved Saline and Preclusion of Tight Junction]

FIG. 4(A) shows histological findings of intestinal mucosal damage. Features, such as shortening or loss, of intestinal villi were recognized in the saline group but were relieved in the H2 group. Furthermore, expression of intestinal tight junction protein ZO-1 was investigated by fluorescent antibody staining. As shown in FIG. 4(B), ZO-1 is localized in the intestinal epithelial tight junction and appears, in the figure, as a series of bright green spots (brightly lighting portion) in the terminal compartment of cell binding site. In the saline group, the localization of ZO-1 was destroyed and light green spots were lost. In contrast, in the H2 group, the localization of ZO-1 was recognized.

[Control of Change in Intestinal Microbiome by Supersaturated Hydrogen Dissolved Saline]

FIG. 5A shows a large number of cell classification groups from feces samples determined by 16S rRNA analysis. In a healthy mouse, the bacterial flora is composed of S24-7 group or the Clostridiaceae bacteria and Lactobacilaceae and Lacnospiraceae bacteria. In contrast, in the saline group, the microbial composition significantly changed on day 1 from CLP, in particular, a dynamic increase in the family Enterobacteriaceae was observed. In the H2 group, the family Enterobacteriaceae was highly suppressed from excessively increasing. The results of quantitative analysis demonstrated that the bacterial count of the family Enterobacteriaceae increased to about $10^5$ on day 1 in the saline group but was considerably suppressed in the H2 group (FIG. 5B).

[Reduction in Oxidation Stress by Supersaturated Hydrogen Dissolved Saline]

Tissue levels of MDA were measured 6 hours after CLP for analysis of oxidative stress. Although there were no differences in MDA levels between the three groups, the MDA level in the H2 group was relatively low compared with those in the other two groups (FIG. 6).

[Decrease of Inflammatory Response in Intestinal Tissue by Supersaturated Hydrogen Dissolved Saline]

The mRNA expressions of inflammatory mediators in intestinal tissue were measured 6 hours after CLP by quantitative RT-PCR, and the results demonstrated that the levels of TNF-$\alpha$, IL-1$\beta$, and IL-6 in the saline group were considerably high compared with those in the pseudo-group (FIG. 7). In the saline group, the iNOS level also tended to be high. However, in the H2 group, the mRNA expressions of these inflammatory mediators were significantly suppressed ($p<0.05$).

INDUSTRIAL APPLICABILITY

The present invention can suppress or prevent (or preclude) bacterial translocation, which is abnormality in the intestinal environment, and therefore allows further preclusion, suppression, or improvement of development or worsening of sepsis, systemic inflammatory response syndrome (SIRS), or multiple organ failure (MOF) syndrome.

Prevention or improvement of bacterial species composition abnormality of intestinal flora is, as demonstrated by the animal models described above, obvious from evidence that an abnormal increase of some bacterial species in the intestinal flora of a subject is dramatically suppressed by administration of hydrogen gas or a dissolved hydrogen liquid. The present invention can prevent or suppress bacterial species composition abnormality of intestinal flora, which is abnormality in the intestinal environment, in a subject and therefore can prevent, relieve, or improve dysbiosis-related diseases.

SEQUENCE LISTING FREE TEXT

SEQ ID NOs: 1 to 12: Primer

All the publications, patents, and patent applications cited in the present specification are incorporated herein by reference in their entirety.

The invention claimed is:

1. A method of suppressing or preventing bacterial translocation in the intestinal environment in a subject, comprising administering to a subject in need thereof a composition comprising dissolved hydrogen as an active ingredient, such that bacterial translocation is suppressed or prevented in the intestinal environment of the subject.

2. The method according to claim 1, wherein the bacterial translocation leads to development or worsening of sepsis, systemic inflammatory response syndrome (SIRS), and multiple organ failure (MOF) syndrome.

3. The method according to claim 1, wherein the composition improves intestinal tissue damage of the subject.

4. The method according to claim 1, wherein the composition is in the form of a hydrogen-dissolved liquid.

5. The method according to claim 4, wherein the hydrogen-dissolved liquid has a hydrogen concentration of 1 to 10 ppm.

6. The method according to claim 1, wherein the composition is administered to the subject by an oral route.

7. The method according to claim 1, wherein the composition is produced in situ using a device for preparing hydrogen-dissolved liquids at the time of administration.

8. The method according to claim 1, wherein suppression of the bacterial translocation leads to: (1) suppressing bacterial species composition abnormality of intestinal flora; and/or (2) suppressing or improving development or worsening of sepsis, systemic inflammatory response syndrome (SIRS), and multiple organ failure (MOF) syndrome.

9. The method according to claim 8, wherein the bacterial species composition abnormality is an abnormal increase or decrease in at least one bacterial species in the intestinal flora.

10. The method according to claim 8, wherein the bacterial species composition abnormality leads to development of a dysbiosis-related disease.

* * * * *

UNITED STATES PATENT AND TRADEMARK OFFICE
CERTIFICATE OF CORRECTION

PATENT NO. : 11,026,967 B2
APPLICATION NO. : 16/085050
DATED : June 8, 2021
INVENTOR(S) : Mitsunori Ikeda et al.

Page 1 of 1

It is certified that error appears in the above-identified patent and that said Letters Patent is hereby corrected as shown below:

On the Title Page

After item "(65) Prior Publication Data", insert:
--(30) Foreign Application Priority Data
Dec. 19, 2017 (JP).....................2017-242401
Dec. 19, 2017 (JP).....................2017-242471--

Signed and Sealed this
Twenty-fourth Day of August, 2021

Drew Hirshfeld
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 12

<210> SEQ ID NO 1
<211> LENGTH: 18
<212> TYPE: DNA
<213> ORGANISM: Artificial
<220> FEATURE:
<223> OTHER INFORMATION: primer

<400> SEQUENCE: 1
aggattagat accctggt                                                 18

<210> SEQ ID NO 2
<211> LENGTH: 17
<212> TYPE: DNA
<213> ORGANISM: Artificial
```

-continued

```
<220> FEATURE:
<223> OTHER INFORMATION: primer

<400> SEQUENCE: 2
crrcacgagc tgacgac                                                    17

<210> SEQ ID NO 3
<211> LENGTH: 23
<212> TYPE: DNA
<213> ORGANISM: Artificial
<220> FEATURE:
<223> OTHER INFORMATION: primer

<400> SEQUENCE: 3
tgccgtaact tcgggagaag gca                                             23

<210> SEQ ID NO 4
<211> LENGTH: 22
<212> TYPE: DNA
<213> ORGANISM: Artificial
<220> FEATURE:
<223> OTHER INFORMATION: primer

<400> SEQUENCE: 4
tcaaggacca gtgttcagtg tc                                              22

<210> SEQ ID NO 5
<211> LENGTH: 20
<212> TYPE: DNA
<213> ORGANISM: Artificial
<220> FEATURE:
<223> OTHER INFORMATION: primer

<400> SEQUENCE: 5
ggcagcctgt gagacctttg                                                 20

<210> SEQ ID NO 6
<211> LENGTH: 21
<212> TYPE: DNA
<213> ORGANISM: Artificial
<220> FEATURE:
<223> OTHER INFORMATION: primer

<400> SEQUENCE: 6
gcattggaag tgaagcgttt c                                               21

<210> SEQ ID NO 7
<211> LENGTH: 22
<212> TYPE: DNA
<213> ORGANISM: Artificial
<220> FEATURE:
<223> OTHER INFORMATION: primer

<400> SEQUENCE: 7
gagaagaggc tgagacatag gc                                              22

<210> SEQ ID NO 8
<211> LENGTH: 22
<212> TYPE: DNA
<213> ORGANISM: Artificial
<220> FEATURE:
<223> OTHER INFORMATION: primer

<400> SEQUENCE: 8
ggttctgtcc ctttcactca ct                                              22
```

```
<210> SEQ ID NO 9
<211> LENGTH: 19
<212> TYPE: DNA
<213> ORGANISM: Artificial
<220> FEATURE:
<223> OTHER INFORMATION: primer

<400> SEQUENCE: 9
tttgaagttg acggacccc                                                    19

<210> SEQ ID NO 10
<211> LENGTH: 22
<212> TYPE: DNA
<213> ORGANISM: Artificial
<220> FEATURE:
<223> OTHER INFORMATION: primer

<400> SEQUENCE: 10
atctccacag ccacaatgag tg                                                22

<210> SEQ ID NO 11
<211> LENGTH: 24
<212> TYPE: DNA
<213> ORGANISM: Artificial
<220> FEATURE:
<223> OTHER INFORMATION: primer

<400> SEQUENCE: 11
tcggaggctt aattacacat gttc                                              24

<210> SEQ ID NO 12
<211> LENGTH: 22
<212> TYPE: DNA
<213> ORGANISM: Artificial
<220> FEATURE:
<223> OTHER INFORMATION: primer

<400> SEQUENCE: 12
tgccattgca caactctttt ct                                                22
```